US009474464B2

(12) United States Patent
Iwai et al.

(10) Patent No.: US 9,474,464 B2
(45) Date of Patent: Oct. 25, 2016

(54) X-RAY IMAGE DIAGNOSTIC APPARATUS

(71) Applicant: Toshiba Medical Systems Corporation, Otawara-shi (JP)

(72) Inventors: Haruki Iwai, Tochigi-ken (JP); Shingo Abe, Tochigi-ken (JP); Shumpei Ohashi, Tochigi-ken (JP); Satoru Ohishi, Tochigi-ken (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 36 days.

(21) Appl. No.: 13/782,196

(22) Filed: Mar. 1, 2013

(65) Prior Publication Data

US 2013/0237810 A1    Sep. 12, 2013

(30) Foreign Application Priority Data

Mar. 6, 2012  (JP) ................................ 2012-049834
Dec. 25, 2012  (JP) ................................ 2012-281740

(51) Int. Cl.
| | |
|---|---|
| A61B 5/05 | (2006.01) |
| G21K 4/00 | (2006.01) |
| H05G 1/62 | (2006.01) |
| A61B 5/06 | (2006.01) |
| A61B 6/03 | (2006.01) |
| A61B 6/06 | (2006.01) |
| A61B 6/00 | (2006.01) |

(52) U.S. Cl.
CPC ............... *A61B 5/061* (2013.01); *A61B 5/062* (2013.01); *A61B 6/032* (2013.01); *A61B 6/06* (2013.01); *A61B 6/542* (2013.01); *A61B 6/5258* (2013.01)

(58) Field of Classification Search
CPC ........................ A61B 2019/2215; A61B 19/22
USPC ............. 600/424-425; 378/41-42, 98-98.12
See application file for complete search history.

(56) References Cited

U.S. PATENT DOCUMENTS

| | | | |
|---|---|---|---|
| 6,208,883 B1 * | 3/2001 | Holupka et al. ............... 600/407 |
| 7,505,549 B2 * | 3/2009 | Ohishi et al. ...................... 378/4 |
| 7,778,685 B2 * | 8/2010 | Evron et al. ................... 600/424 |
| 7,920,911 B2 * | 4/2011 | Hoshino et al. ............... 600/423 |
| 2003/0088179 A1 * | 5/2003 | Seeley et al. .................. 600/424 |
| 2004/0097804 A1 * | 5/2004 | Sobe .............................. 600/424 |
| 2004/0138548 A1 * | 7/2004 | Strommer et al. ............ 600/407 |
| 2005/0033149 A1 * | 2/2005 | Strommer et al. ............ 600/407 |
| 2005/0085720 A1 * | 4/2005 | Jascob et al. .................. 600/424 |

(Continued)

*Primary Examiner* — John P Leubecker
*Assistant Examiner* — Arnaldo Torres Diaz
(74) *Attorney, Agent, or Firm* — Oblon, McClelland, Maier & Neustadt, L.L.P

(57) ABSTRACT

An X-ray image diagnostic apparatus includes an X-ray imager, an image data generator, a position information acquisition mechanism, a position information corrector, and a display. The X-ray imager generates projection data by X-ray imaging in first and second imaging modes for a patient. The image data generator generates reference image data based on projection data in the first imaging mode and image data for positional deviation correction based on projection data in the second imaging mode. The position information acquisition mechanism acquires position information of a treatment device inserted into the patient. The position information corrector corrects the position information of the treatment device based on the position information of the treatment device and treatment device information of the image data for positional deviation correction, collected by X-ray imaging in the second imaging mode. The display displays the reference image data to which the corrected position information is added.

10 Claims, 7 Drawing Sheets

(56) References Cited

U.S. PATENT DOCUMENTS

| | | | |
|---|---|---|---|
| 2007/0100223 A1* | 5/2007 | Liao et al. | 600/407 |
| 2007/0238985 A1* | 10/2007 | Smith et al. | 600/424 |
| 2008/0183071 A1* | 7/2008 | Strommer et al. | 600/424 |
| 2008/0221435 A1* | 9/2008 | Rasche | 600/424 |
| 2008/0221439 A1* | 9/2008 | Iddan et al. | 600/424 |
| 2008/0319312 A1* | 12/2008 | Eichler | A61B 5/06 600/424 |
| 2010/0274120 A1* | 10/2010 | Heuscher | 600/424 |
| 2010/0312038 A1* | 12/2010 | Shechter | 600/3 |
| 2011/0082366 A1* | 4/2011 | Scully et al. | 600/424 |
| 2012/0087562 A1* | 4/2012 | Isaacs | G06F 19/321 382/131 |
| 2013/0113791 A1* | 5/2013 | Isaacs | G06T 11/60 345/419 |
| 2013/0243153 A1* | 9/2013 | Sra | A61B 6/022 378/41 |

* cited by examiner

X-RAY IMAGE DIAGNOSTIC APPARATUS

CROSS-REFERENCE TO RELATED APPLICATION

This application is based upon and claims the benefit of priority from Japanese Patent Application No. 2012-049834, filed on Mar. 6, 2012; the entire contents of which are incorporated herein by reference.

BACKGROUND OF THE INVENTION

1. Field of the Invention

The present invention relates to a technique of an X-ray image diagnostic apparatus.

2. Background Art

Medical image diagnosis using an X-ray image diagnostic apparatus, an X-ray CT (Computed Tomography) apparatus, or the like has rapidly progressed with the development of computer technology, and has become indispensable in today's medical treatment. In particular, X-ray image diagnosis of cardiovascular region, which has progressed with the development of the catheter procedure, is widely used for the arteries and veins of the whole body including a cardiovascular system.

The X-ray image diagnostic apparatus for the diagnosis of cardiovascular region includes an X-ray generation unit and an X-ray detection unit (hereinafter, these are referred to collectively as an imaging system), a holding unit such as a C arm that holds an imaging system, a top plate on which a patient is placed, and the like. By moving the imaging system fixed to the top plate or the holding unit in a desired direction, it is possible to perform X-ray imaging from an optimal direction for a treatment site of the patient.

On the other hand, minimally invasive treatment called MIT has been drawing attention in recent years. As a representative MIT for a patient with heart disease or ischemic brain disease, a so-called intervention treatment that uses a catheter or the like under observation of the image data may be mentioned.

Examples of a device for endovascular treatment (hereinafter, referred to as a treatment device) used in the treatment of cerebral blood vessel, cardiac blood vessel, peripheral blood vessel, and the like in which stenosis has occurred due to the deposition of cholesterol on the inner wall include a balloon catheter which expands a stenotic portion in a radial direction, a stent for maintaining the blood vessel diameter expands by the balloon, and DCA (directional coronary atherectomy) or a rotablator which excises the plaque of a stenotic portion by moving or rotating a micro cutter fixed to the tip of the catheter within the blood vessel.

In addition, a method has been adopted in which the position of such a treatment device in the blood vessel is specified by observing the image data obtained in real time when continuously performing X-ray imaging in a fluoroscopic imaging mode for a patient to whom the treatment device is inserted.

According to such a method, however, X-ray irradiation to the patient is performed over a long period of time. Therefore, there has been a problem in that the exposure dose increases. In addition, in order to solve such a problem, a method has been adopted in which, for example, one item of image data (reference image data) is collected by X-ray imaging for a patient to whom a contrast agent is injected and then the position information of a treatment device, which is supplied in time series from a position detector of the treatment device inserted into the body of the patient, is sequentially superimposed on the reference image data, and the result is displayed.

According to the above-described method of superimposing the position information of the treatment device measured separately on the reference image data collected in advance and displaying the result, it is possible to significantly reduce the exposure dose to the patient during medical treatment. However, since the position detector provided in the treatment device does not usually have sufficient accuracy, there is a problem in that it is difficult to correctly check the position information of the treatment device inserted into the blood vessel.

DETAILED DESCRIPTION OF THE INVENTION

First, an X-ray image diagnostic apparatus according to the present embodiment generates positional deviation correction data (hereinafter, referred to as correction data) by comparing the treatment device information of image data for positional deviation correction, which is collected by X-ray imaging in a positional deviation correction imaging mode, for a patient to whom a treatment device such as a stent or a guide wire is inserted with the position information of the treatment device measured separately. Then, the X-ray image diagnostic apparatus generates display data effective for the monitoring of the treatment device (hereinafter, referred to as display data for treatment device monitoring) by performing positional deviation correction for the position information of the treatment device, which is measured in time series after the measurement of the position information, using the correction data and adding the position information after the positional deviation correction to reference image data collected in advance by performing X-ray imaging in a stationary imaging mode for the patient.

Configuration and Function of Apparatus

The configuration and function of an X-ray image diagnostic apparatus according to the present embodiment will be described with reference to FIGS. 1 to 6. In addition, FIG. 1 is a schematic diagram showing the overall configuration of the X-ray image diagnostic apparatus according to the present embodiment, and FIGS. 2 to 4 and 6 are schematic diagrams showing the specific configuration of an X-ray imaging unit, a high voltage control unit, a device information detection unit, and an imaging timing setting unit that are provided in the X-ray image diagnostic apparatus.

Figure 1:
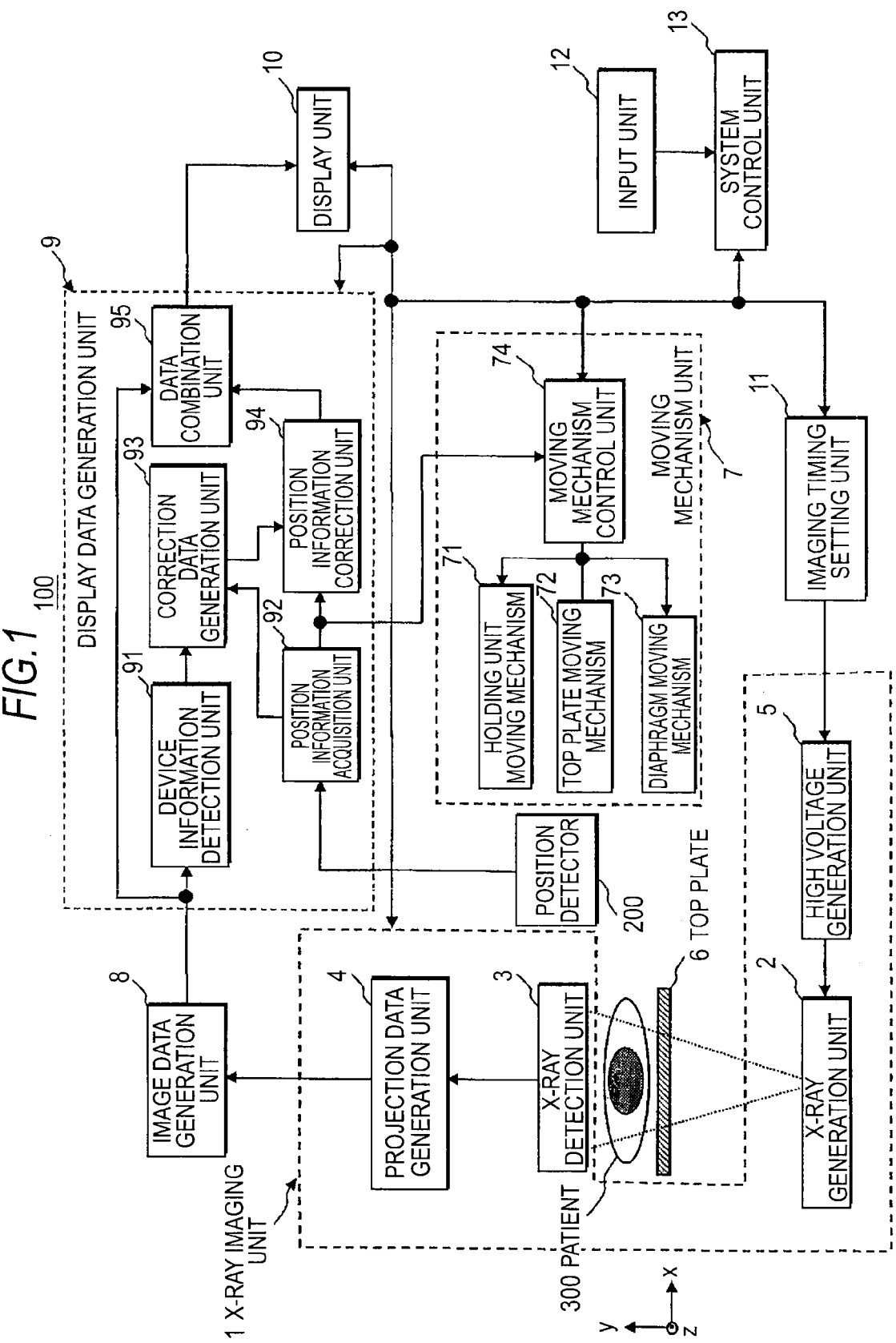
FIG. 1 is a schematic diagram showing the overall configuration of an X-ray image diagnostic apparatus according to the present embodiment.

An X-ray image diagnostic apparatus 100 shown in FIG. 1 includes: an X-ray imaging unit 1 that generates projection data by irradiating the imaging region including a treatment site of a patient 300 with X-rays in the stationary imaging mode (first imaging mode) and the positional deviation correction imaging mode (second imaging mode) and detecting X-rays transmitted through the imaging region; a holding unit (not shown) that holds an imaging system capable of performing the X-ray irradiation and the X-ray detection described above; a top plate 6 on which the patient 300 is placed; a moving mechanism unit 7 that moves the holding unit to which the imaging system is fixed, the top plate 6 on which the patient 300 is placed, and a movable diaphragm 22 provided in an X-ray generation unit 2, which will be described later, to a desired position; and an image data generation unit 8 that generates standard image data and image data for positional deviation correction using the projection data in the stationary imaging mode and the positional deviation correction imaging mode output from the X-ray imaging unit 1. In addition, the X-ray image diagnostic apparatus 100 further includes: a display data generation unit 9 that generates display data for treatment device monitoring by performing positional deviation correction for the position information of the treatment device supplied sequentially from a position detector 200 using the correction data, which is generated by comparing the treatment device information of the image data for positional deviation correction collected at the imaging timing satisfying a predetermined timing condition with the position information of the treatment device supplied from the position detector 200 of the treatment device, and adding the corrected position information of the treatment device to the reference image data; a display unit 10 that displays the display data for treatment device monitoring generated by the display data generation unit 9; an imaging timing setting unit 11 that sets an imaging timing in the positional deviation correction imaging mode; an input unit 12 that performs input of patient information, selection of the stationary imaging mode and the positional deviation correction imaging mode, setting of the X-ray irradiation conditions or the image data generation conditions in these imaging modes, setting of the display data generation conditions for treatment device monitoring, input of various instruction signals, and the like; and a system control unit 13 that performs overall control of each of the units described above.

As shown in FIG. 1, the X-ray imaging unit 1 includes the X-ray generation unit 2 and an X-ray detection unit 3 that form an imaging system, a projection data generation unit 4, and a high voltage generation unit 5, and has a function of irradiating the imaging region of the patient 300 with X-rays and a function of generating projection data by detecting X-rays transmitted through the imaging region.

As the position detector 200, for example, a GPS (Global Positioning System) or a magnetic sensor is used. When a magnetic sensor is used, the magnetic sensor detects a magnetic field generated by a magnetic field generation unit (not shown) and processes an electric signal based on the detected magnetic field. Then, the position detector 200 acquires the position information of the treatment device on the basis of a distance between the magnetic sensor and the magnetic field generation unit.

Figure 2:
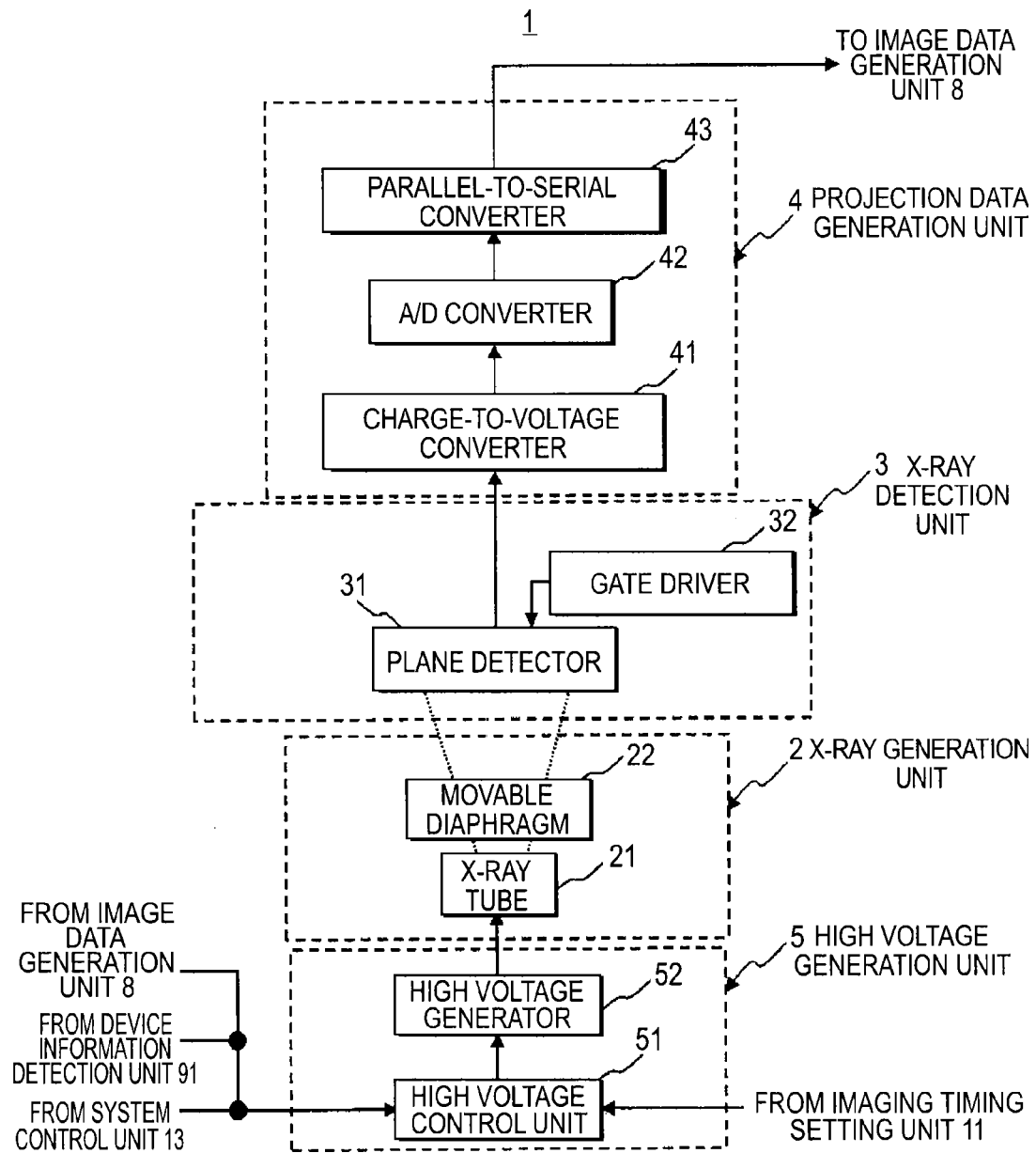
FIG. 2 is a schematic diagram showing the specific configuration of an X-ray imaging unit provided in the X-ray image diagnostic apparatus according to the present embodiment.

FIG. 2 is a schematic diagram showing the specific configuration of each of the above-described units provided in the X-ray imaging unit 1. The X-ray generation unit 2 includes an X-ray tube 21, which irradiates the imaging region of the patient 300 with X-rays, and the movable diaphragm 22, which forms cone beams in a predetermined range for the X-rays emitted from the X-ray tube 21. The X-ray tube 21 is a vacuum tube that generates X-rays, and generates X-rays by accelerating thermal electrons, which are generated from the heated cathode (filament), with a DC high voltage supplied from the high voltage generation unit 5 and making the thermal electrons collide with a tungsten anode.

On the other hand, the movable diaphragm 22 is used to reduce the exposure dose to the patient 300 and improve the image quality of image data, and includes: an upper blade that narrows X-rays emitted from the X-ray tube 21 to a predetermined irradiation range; a lower blade that moves in conjunction with the upper blade to reduce the amount of scattered rays or leaking rays; and a compensation filter (not shown) that prevents halation by selectively reducing X-rays transmitted through a medium whose absorption amount is small.

In particular, the X-ray irradiation range in the positional deviation correction imaging mode in the present embodiment is determined by the diaphragm blade (upper blade) of the movable diaphragm 22 whose position is controlled on the basis of the position information of the treatment device supplied from the position detector 200 of the treatment device inserted into the body of the patient 300. Accordingly, it is possible to reduce the exposure dose to the patient 300 by limiting the X-ray irradiation range to a relatively narrow region around the treatment device.

On the other hand, the X-ray detection unit 3 uses a method that uses an image intensifier and an X-ray TV and a method that uses a plane detector. In addition, there are plane detectors based on a method of directly converting X-rays into electric charges and a method of converting X-rays into electric charges after converting the X-rays into light. Although the X-ray detection unit 3 having a plane detector capable of directly converting X-rays into electric charges is described herein, it is not limited to this.

That is, as shown in FIG. 2, the X-ray detection unit 3 according to the present embodiment includes a plane detector 31 that detects X-rays transmitted through the patient 300 and a gate driver 32 that supplies to the plane detector 31a driving signal for reading the detected X-rays as signal charges.

The plane detector 31 is formed by arraying fine detection elements in a two-dimensional manner in column and row directions. Each detection element includes: a photoelectric film (not shown) that detects X-rays and generates signal charges according to the amount of incident X-rays; a charge storage capacitor (not shown) that stores signal charges generated by the photoelectric film; and a TFT (Thin Film Transistor) (not shown) that reads the signal charges stored in the charge storage capacitor at the predetermined timing.

The projection data generation unit 4 includes: a charge-to-voltage converter 41 that converts signal charges read from the plane detector 31 in parallel, for example, in row-direction units into a voltage; an A/D converter 42 that converts the output of the charge-to-voltage converter 41 into a digital signal (data elements of projection data); and a parallel-to-serial converter 43 that converts the digital-converted data elements into time-series data elements. Then, the time-series data elements output from the parallel-to-serial converter 43 are supplied to the image data generation unit 8 shown in FIG. 1.

On the other hand, the high voltage generation unit 5 includes: a high voltage generator 52 that generates a high voltage, which is applied between the anode and the cathode, in order to accelerate thermal electrons generated from the cathode of the X-ray tube 21; and a high voltage control unit 51 that controls a tube current, a tube voltage, a high voltage application time, a high voltage application timing, and the like in the high voltage generator 52 on the basis of the X-ray irradiation conditions in the stationary imaging mode and the positional deviation correction imaging mode, which are supplied from the system control unit 13, and the imaging timing signal supplied from the imaging timing setting unit 11.

In particular, the high voltage control unit 51 according to the present embodiment performs so-called ABC (Auto Brightness Control) to control the tube current or the tube voltage of the high voltage generator 52, so that the average pixel value of a region of interest (hereinafter, referred to as a pixel value evaluation region), which is set to image data for positional deviation correction so as to correspond to the X-ray irradiation range in the positional deviation correction imaging mode, becomes a predetermined value.

Figure 3:
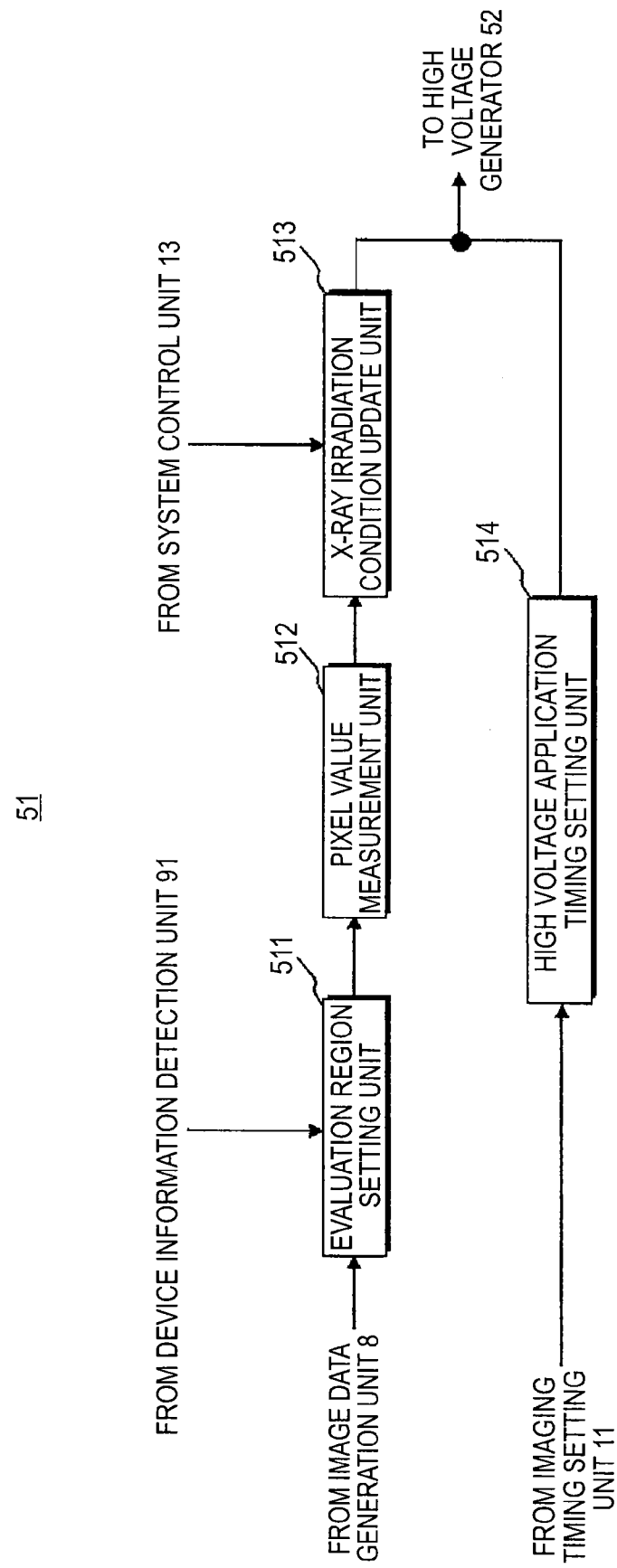
FIG. 3 is a schematic diagram showing the specific configuration of a high voltage control unit provided in the X-ray image diagnostic apparatus according to the present embodiment.

For example, as shown in FIG. 3, the high voltage control unit 51 includes: an evaluation region setting unit 511 that sets a pixel value evaluation region with a predetermined size around the treatment device, for the image data for positional deviation correction read from the image data storage unit of the image data generation unit 8, on the basis of the treatment device information that a device information detection unit 91 of the display data generation unit 9 has detected for the image data for positional deviation correction collected in advance; a pixel value measurement unit 512 that measures the average pixel value of the pixel value evaluation region in the image data for positional deviation correction; an X-ray irradiation condition update unit 513 that updates the X-ray irradiation conditions (that is, the tube voltage, tube current, high voltage application time, and the like of the high voltage generator 52) in the positional deviation correction imaging mode, which are supplied through the system control unit 13 from the input unit 12, on the basis of the average pixel value supplied from the pixel value measurement unit 512; and a high voltage application timing setting unit 514 that sets a high voltage application timing in the positional deviation correction imaging mode on the basis of the imaging timing signal supplied from the imaging timing setting unit 11.

Then, by generating subsequent image data for positional deviation correction according to the X-ray irradiation conditions updated by the X-ray irradiation condition update unit 513, it is possible to collect satisfactory image data for positional deviation correction in the treatment device and the surrounding region. As a result, the treatment device information shown in the image data for positional deviation correction can be detected with high accuracy.

Referring back to FIG. 1, the moving mechanism unit 7 includes: a holding unit moving mechanism 71 that rotates or moves a holding unit (not shown), to which the X-ray generation unit 2 and the X-ray detection unit 3 (imaging system) are fixed, around the patient 300; a top plate moving mechanism 72 that moves the top plate 6 in a body axis direction (z direction in FIG. 1) of the patient 300 and directions (x and y directions in FIG. 1) perpendicular to the body axis; a diaphragm moving mechanism 73 that moves a diaphragm blade of the movable diaphragm 22, which is provided in the X-ray generation unit 2, to a predetermined position; and a moving mechanism control unit 74 that controls the holding unit moving mechanism 71, the top plate moving mechanism 72, and the diaphragm moving mechanism 73.

In addition, the moving mechanism control unit 74 supplies a movement control signal, which is generated on the basis of an imaging system movement instruction signal supplied through the system control unit 13 from the input unit 12, to the holding unit moving mechanism 71, and sets the imaging position and the imaging direction in X-ray imaging by rotating or moving the holding unit, to which the imaging system is fixed, around the patient 300.

Similarly, the moving mechanism control unit 74 supplies a movement control signal, which is generated on the basis of a top plate movement instruction signal supplied through the system control unit 13 from the input unit 12, to the top plate moving mechanism 72, and sets the center of the imaging region by moving the top plate 6 in parallel in the body axis direction of the patient 300 or in a direction perpendicular to the body axis.

In addition, the moving mechanism control unit 74 supplies to the diaphragm moving mechanism 73 a movement control signal supplied from the system control unit 13, and sets the X-ray irradiation range in the stationary imaging mode and the positional deviation correction imaging mode to have a predetermined size by moving the plurality of diaphragm blades, which are provided in the movable diaphragm 22 of the X-ray generation unit 2, to predetermined positions. In particular, in the positional deviation correction imaging mode of the present embodiment, a movement control signal for forming an X-ray irradiation range having a predetermined size, which is a relatively narrow range around the treatment device, for the patient 300 is supplied to the diaphragm moving mechanism 73 on the basis of the position information of the treatment device supplied from the position detector 200 of the treatment device.

Then, the image data generation unit 8 includes a projection data storage unit, an image data processing unit, and an image data storage unit (not shown). Data elements of the projection data output in time series from the projection data generation unit 4 of the X-ray imaging unit 1 in the stationary imaging mode and the positional deviation correction imaging mode are stored in the projection data storage unit so as to correspond to the column and row directions of the detection elements, and wide-range reference image data and narrow-range image data for positional deviation correction based on the treatment device information are generated.

On the other hand, the image data processing unit performs a filtering process or the like on the reference image data and the image data for positional deviation correction read from the projection data storage unit in order to remove noise, and stores the reference image data and the image data for positional deviation correction after the processing in the image data storage unit.

As shown in FIG. 1, the display data generation unit 9 includes the device information detection unit 91, a position information acquisition unit 92, a correction data generation unit 93, a position information correction unit 94, and a data combination unit 95.

Figure 4:
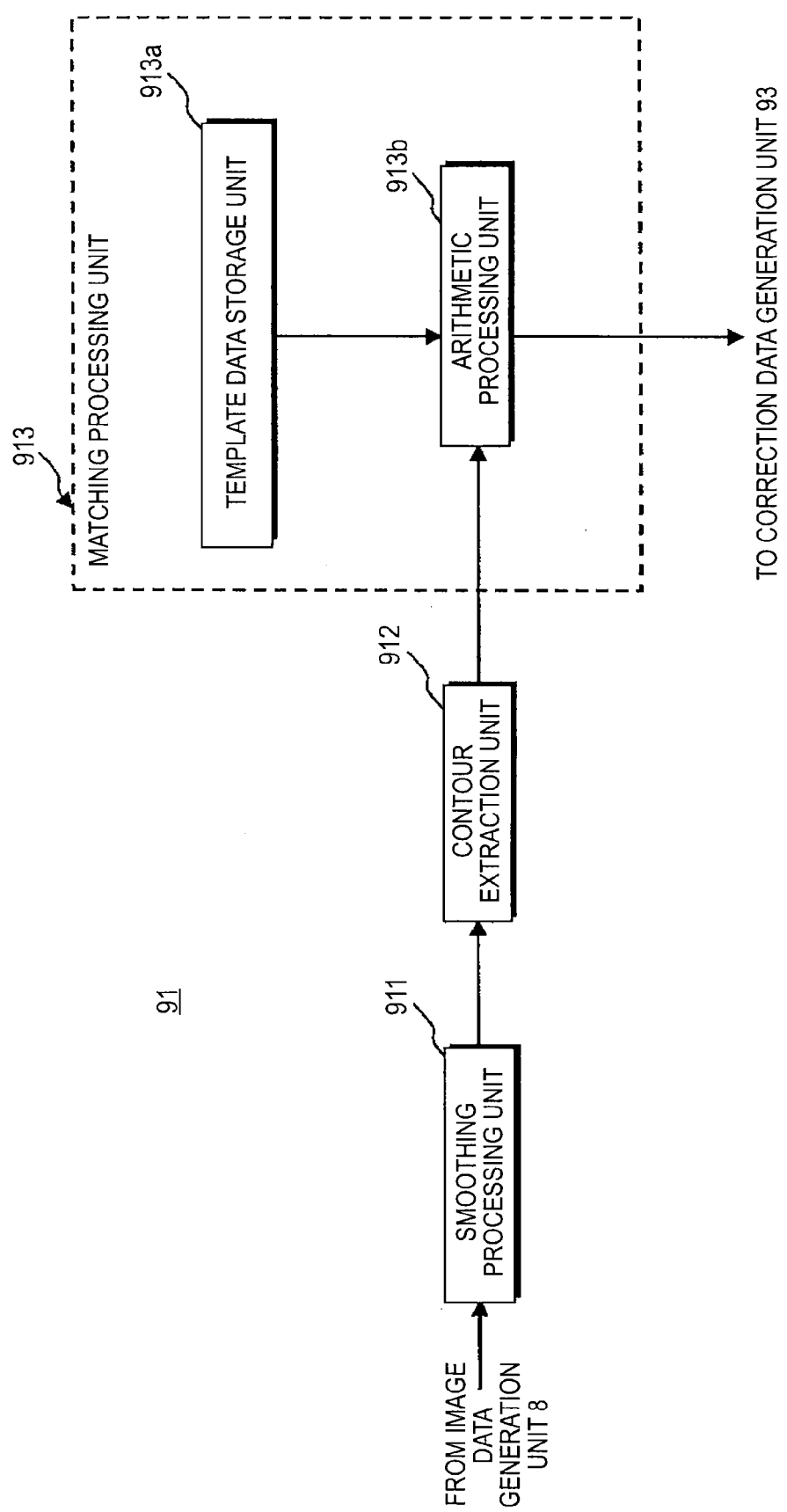
FIG. 4 is a schematic diagram showing the specific configuration of a device information detection unit provided in the X-ray image diagnostic apparatus according to the present embodiment.

FIG. 4 is a schematic diagram showing the specific configuration of the device information detection unit 91 provided in the display data generation unit 9. As shown in FIG. 4, the device information detection unit 91 includes a smoothing processing unit 911, a contour extraction unit 912, and a matching processing unit 913, for example.

The smoothing processing unit 911 removes noise by performing a filtering process to smooth the image data for positional deviation correction supplied from the image data generation unit 8 in X-ray imaging in the positional deviation correction imaging mode, and the contour extraction unit 912 performs image processing to extract a contour from the image data for positional deviation correction after the smoothing processing.

The matching processing unit 913 includes a template data storage unit 913a and an arithmetic processing unit 913b. In the template data storage unit 913a, template data corresponding to the shapes of various treatment devices is stored in advance together with treatment device identification information as supplementary information.

On the other hand, the arithmetic processing unit 913b reads template data, which corresponds to the treatment device used for the medical treatment, from various kinds of template data, which are stored in the template data storage unit 913a, on the basis of the treatment device identification information, and detects treatment device information included in the image data for positional deviation correction by pattern matching processing between the template data and the image data for positional deviation correction after contour extraction supplied from the contour extraction unit 912.

Referring back to FIG. 1, the position information acquisition unit 92 of the display data generation unit 9 receives the position information of the treatment device supplied from the position detector 200 of the treatment device (not shown) inserted into the blood vessel of the patient 300.

On the other hand, the correction data generation unit detects the positional deviation of treatment device position information for the treatment device information by comparing the treatment device information of the image data for positional deviation correction, which is supplied from the matching processing unit 913 of the device information detection unit 91, with the position information of the treatment device, which is supplied from the position information acquisition unit 92, and generates correction data for correcting the positional deviation for the position information of the treatment device on the basis of this detection result. Then, the generated correction data is stored in a correction data storage unit (not shown) of the correction data generation unit 93.

Then, the position information correction unit 94 corrects the positional deviation for the position information of the treatment device, which is supplied in time series through the position information acquisition unit 92 from the position detector 200 of the treatment device, using the correction data read from the correction data storage unit of the correction data generation unit 93, and the data combination unit 95 generates display data for treatment device monitoring by superimposing the position information of the treatment device whose positional deviation has been corrected by the position information correction unit 94 on the reference image data read from the image data storage unit of the image data generation unit 8.

Figure 5:
FIG. 5 is a drawing showing a specific example of display data for treatment device monitoring generated by a display data generation unit provided in the X-ray image diagnostic apparatus according to the present embodiment.

FIG. 5 shows a specific example of the display data for treatment device monitoring generated by the display data generation unit 9. The display data for treatment device monitoring is generated by superimposing position information Mx of the treatment device whose positional deviation has been corrected by the position information correction unit 94 on the reference image data Ib generated by the image data generation unit 8 in the stationary imaging mode.

Although the position information Mx in this case is shown using a marker which has a predetermined shape and a different color from the reference image data Ib, the display method is not particularly limited.

The display unit 10 includes a data conversion unit and a monitor which are not shown in the drawings. The data conversion unit converts the display data for treatment device monitoring supplied from the display data generation unit 9 into a predetermined display format, and performs conversion processing, such as D/A conversion or television format conversion, and displays the result on the monitor.

Figure 6:
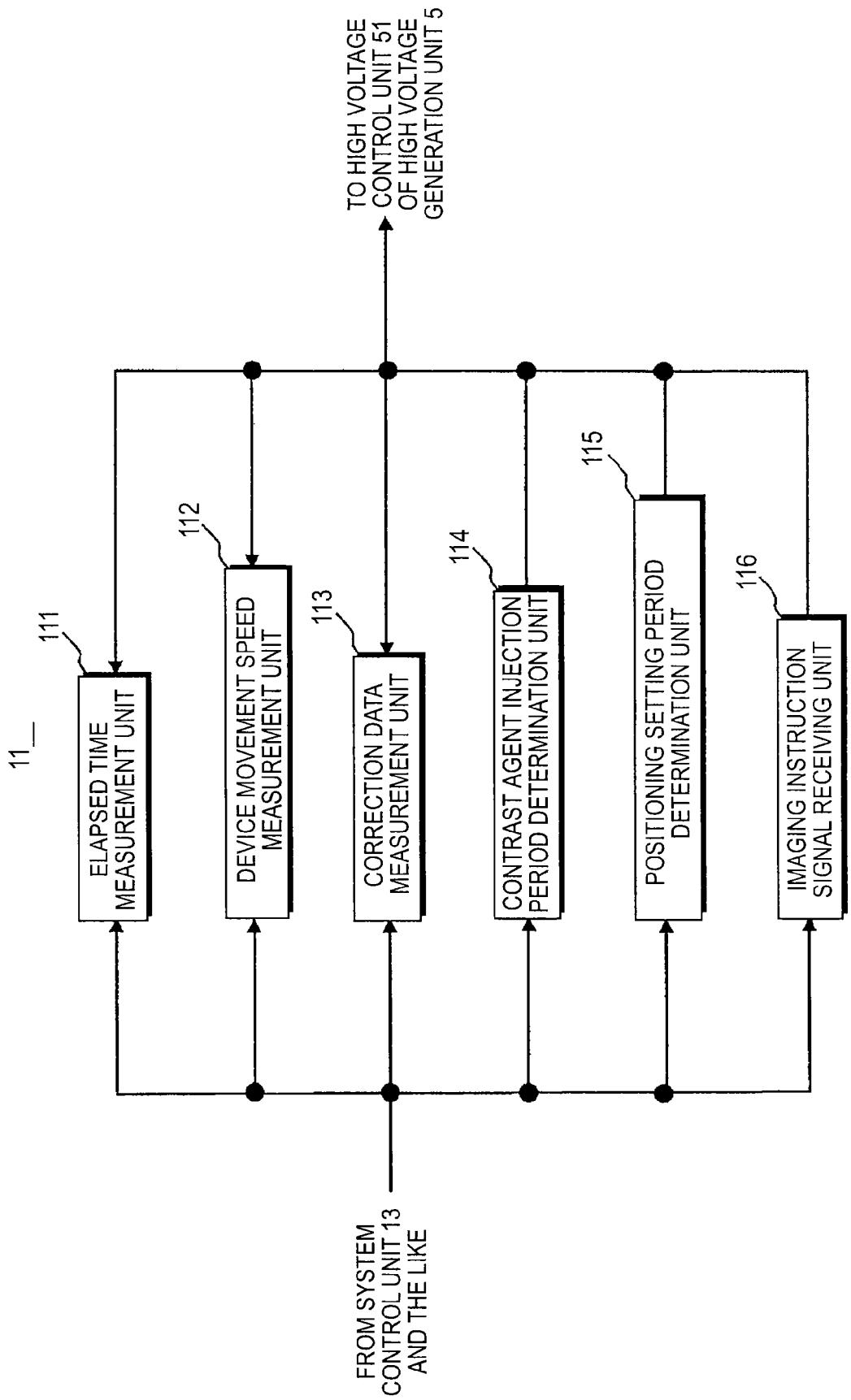
FIG. 6 is a schematic diagram showing the specific configuration of an imaging timing setting unit provided in the X-ray image diagnostic apparatus according to the present embodiment.

In addition, the imaging timing setting unit 11 has a function of setting the imaging timing in the positional deviation correction imaging mode. For example, as shown in FIG. 6, the imaging timing setting unit 11 includes an elapsed time measurement unit 111, a device movement speed measurement unit 112, a correction data measurement unit 113, a contrast agent injection period determination unit 114, a positioning setting period determination unit 115, and an imaging instruction signal receiving unit 116.

The elapsed time measurement unit 111 measures an elapsed time from a start instruction signal of the positional deviation correction imaging mode, which is supplied through the system control unit 13 from the input unit 12, or from imaging timing signals already output from the device movement speed measurement unit 112, the correction data measurement unit 113, and the elapsed time measurement unit 111, and sets the point of time after a predetermined time $\Delta\tau$ has passed from the generation time of the imaging mode start instruction signal or the preceding imaging timing signal as the next imaging timing. Then, the elapsed time measurement unit 111 generates an imaging timing signal corresponding to the imaging timing and supplies the imaging timing signal to the high voltage control unit 51 of the high voltage generation unit 5.

The device movement speed measurement unit 112 receives the position information of the treatment device in the display data for treatment device monitoring, which is supplied in time series from the display data generation unit 9, and measures the movement speed (the amount of movement per unit time) of the treatment device on the basis of the position information. Then, the device movement speed measurement unit 112 sets the point of time, at which the movement speed becomes larger than a predetermined threshold value $\Delta V$, as the next imaging timing, generates an imaging timing signal corresponding to this imaging timing, and supplies the imaging timing signal to the high voltage control unit 51.

The correction data measurement unit 113 receives the correction data generated by the correction data generation unit 93 of the display data generation unit 9, and measures the size of the correction data corresponding to the size of the positional deviation. Then, the correction data measurement unit 113 sets the point of time, at which the size of the measured correction data becomes larger than a predetermined threshold value $\Delta\alpha$, as the next imaging timing, generates an imaging timing signal corresponding to this imaging timing, and supplies the imaging timing signal to the high voltage control unit 51.

On the other hand, the contrast agent injection period determination unit 114 determines an injection period of the contrast agent for the patient 300 on the basis of a contrast agent injection start instruction signal and an contrast agent injection end instruction signal that are input through the input unit 12, for example. Then, when the contrast agent is injected, the generation of imaging timing signals in the elapsed time measurement unit 111, the device movement speed measurement unit 112, and the correction data measurement unit 113 is stopped.

The positioning setting period determination unit 115 determines a setting period of an imaging position or an imaging direction for the patient 300 on the basis of a movement instruction signal and a stop instruction signal for the moving mechanism unit 7 that are input through the input unit 12. Then, when any of the various moving mechanisms provided in the moving mechanism unit 7 is moving, the generation of imaging timing signals in the elapsed time measurement unit 111, the device movement speed measurement unit 112, and the correction data measurement unit 113 is stopped.

When the position information of the treatment device in the display data for treatment device monitoring displayed on the monitor of the display unit 10 is close to the region of interest, such as a blood vessel branch point, the imaging instruction signal receiving unit 116 generates an imaging timing signal corresponding to the imaging instruction signal supplied through the system control unit 13 from the input unit 12 and supplies the imaging timing signal to the high voltage control unit 51.

Next, the input unit 12 shown in FIG. 1 is an interactive interface including input devices, such as a display panel, a keyboard, a track ball, a joystick, and a mouse. The input unit 12 is used to perform input of patient information, selection of the stationary imaging mode and the positional deviation correction imaging mode, setting of the X-ray irradiation conditions or the image data generation conditions in these imaging modes, generation of display data for treatment device monitoring and setting of display conditions, setting of time $\Delta\tau$ and threshold values $\Delta V$ and $\Delta\alpha$ used in the setting of the imaging timing, input of various instruction signals including the imaging mode start instruction signal and the imaging instruction signal, and the like. In particular, when the position information of the treatment device in the display data for treatment device monitoring displayed on the monitor of the display unit 10 is close to the region of interest such as a blood vessel branch point which is important for device insertion, an imaging instruction signal for executing X-ray imaging in the positional deviation correction imaging mode by a predetermined frequency is input.

The system control unit 13 includes a CPU and an input information storage unit that are not shown in the drawings, and various kinds of information input, set, and selected through the input unit 12 are stored in the input information storage unit. In addition, the CPU performs overall control of the above-described units provided in the X-ray image diagnostic apparatus 100 on the basis of such information, and executes the generation of reference image data based on X-ray imaging in the stationary imaging mode, the generation of image data for positional deviation correction based on X-ray imaging in the positional deviation correction imaging mode, and the generation and display of display data for treatment device monitoring based on combination processing of the reference image data and the position information of the treatment device whose positional deviation has been corrected on the basis of the image data for positional deviation correction.

Generation/Display Procedure of Display Data for Treatment Device Monitoring

Next, the generation/display procedure of display data for treatment device monitoring in the present embodiment will be described using the flow chart shown in FIG. 7. In addition, although the imaging timing setting unit 11 that generates a new imaging timing signal according to the elapsed time from the input time of the imaging mode start instruction signal, which is input from the input unit 12 in the positional deviation correction imaging mode, or from the generation time of the preceding imaging timing signal will be described below, the present invention is not limited to this. For example, it is also possible to apply the imaging timing setting unit 11 that generates a new imaging timing signal on the basis of the movement speed of the treatment device, the size of correction data, or the like.

Prior to X-ray imaging in the stationary imaging mode, the operator of the X-ray image diagnostic apparatus 100 performs input of patient information, setting of X-ray irradiation conditions or the image data generation conditions in the stationary imaging mode and the positional deviation correction imaging mode, setting of generation/display conditions of the display data for treatment device monitoring, setting of time $\Delta\tau$ and threshold values $\Delta V$ and $\Delta\alpha$, and the like using the input unit 12. The various kinds of input or set information described above are stored in the input information storage unit provided in the system control unit 13 (step S1 in FIG. 7).

After the above-described initial setting ends, the operator injects a contrast agent into the patient 300 and then selects the stationary imaging mode and inputs an imaging mode start instruction signal using the input unit 12. Then, the generation of reference image data in the stationary imaging mode is started by the supply of the imaging mode start instruction signal to the system control unit 13.

That is, the system control unit 13 that has received the imaging mode start instruction signal input through the input unit 12 supplies the X-ray irradiation conditions in the stationary imaging mode, which are stored in the input information storage unit of the system control unit 13, and the newly generated X-ray generation instruction signal to the high voltage control unit 51 of the high voltage generation unit 5. The high voltage control unit 51 that has received this instruction signal controls the high voltage generator 52 on the basis of the X-ray irradiation conditions and applies a predetermined high voltage to the X-ray tube 21 of the X-ray generation unit 2. Then, the X-ray tube 21 to which a high voltage is applied irradiates an imaging region, which includes a treatment site of the patient 300, with X-rays, and X-rays transmitted through the imaging region are detected by the plane detector 31 of the X-ray detection unit 3 provided after the X-ray tube 21.

In this case, photoelectric films of detection elements that are arrayed in a two-dimensional manner in the plane detector 31 receive the X-rays transmitted through the imaging region, and signal charges proportional to the amount of X-ray transmission are stored in charge storage capacitors. After the X-ray irradiation of a predetermined period ends, the gate driver 32 of the X-ray detection unit 3, to which a clock pulse having a predetermined frequency is supplied from the system control unit 13, supplies a driving pulse to TFTs of the plane detector 31 to sequentially read signal charges stored in the charge storage capacitor.

Then, the read signal charges are converted into a voltage by the charge-to-voltage converter 41 of the projection data generation unit 4 and are further converted into digital signals by the A/D converter 42, and then the result is temporarily stored as projection data for one line in a buffer memory of the parallel-to-serial converter 43. Then, the parallel-to-serial converter 43 serially reads the projection data, which is stored in the buffer memory of the parallel-to-serial converter 43, line by line and stores the projection data sequentially in the projection data storage unit of the image data generation unit 8 to generate two-dimensional reference image data. Then, the image data processing unit of the image data generation unit 8 performs a filtering process on the obtained reference image data in order to remove noise when necessary, and stores the processed reference image data in the image data storage unit of the image data generation unit 8 (step S2 in FIG. 7).

Figure 7:
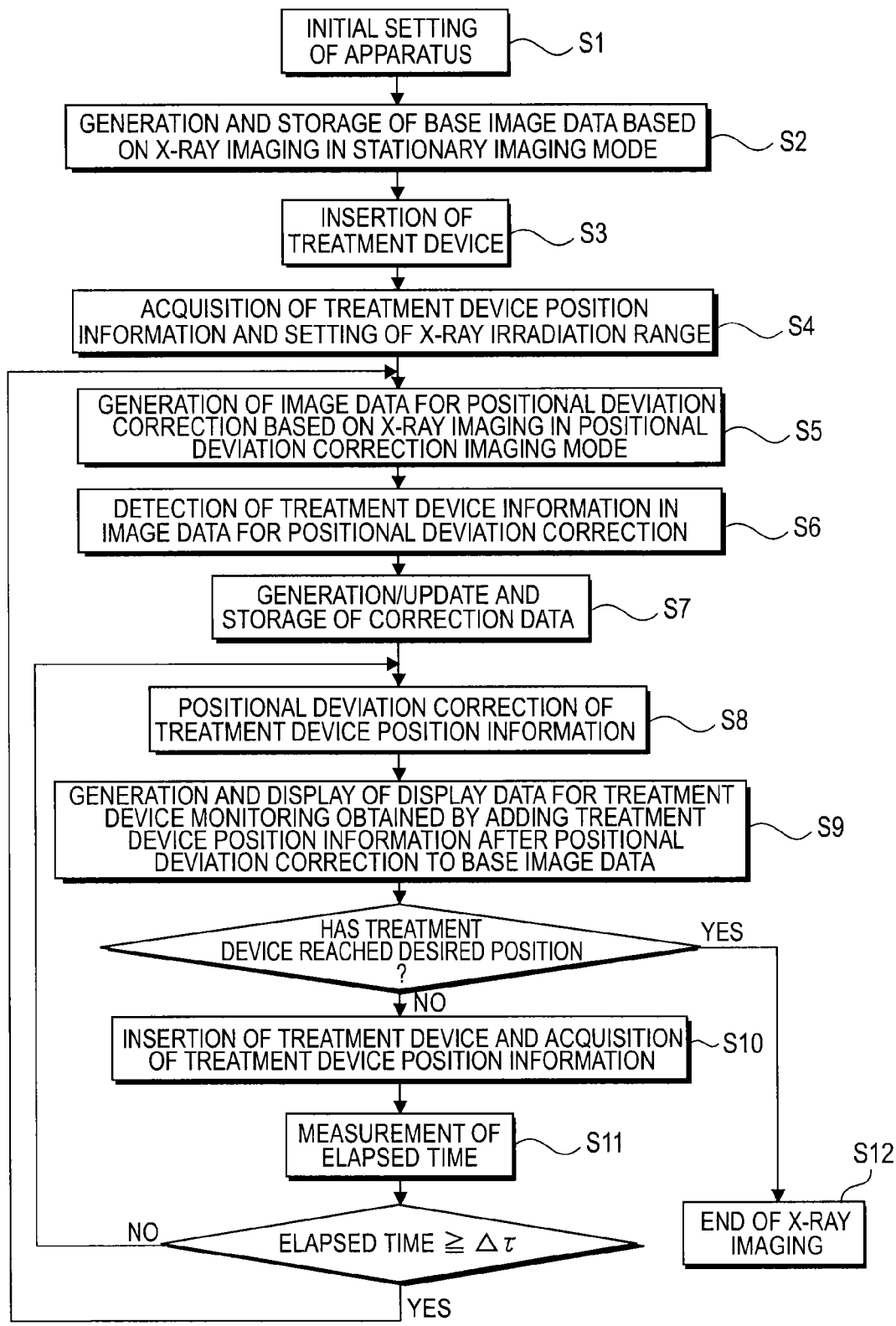
FIG. 7 is a flow chart showing the generation/display procedure of display data for treatment device monitoring in the present embodiment.

After the generation and storage of the reference image data in the stationary imaging mode ends, the operator selects the positional deviation correction imaging mode and inputs an imaging mode start instruction signal using the input unit 12 and then starts the insertion of a treatment devices, such as a stent or a guide wire, into a treatment site of the patient 300 (step S3 in FIG. 7).

Then, the moving mechanism control unit 74 of the moving mechanism unit 7 that has received the imaging mode start instruction signal receives the position information of the treatment device, which is supplied through the position information acquisition unit 92 of the display data generation unit 9 from the position detector 200 of the treatment device inserted into the body of the patient 300, and sets an X-ray irradiation range having a predetermined size, which is a relatively narrow range around the treatment device, for the patient 300 by supplying a movement control signal based on the position information to the moving mechanism unit 73 (step S4 in FIG. 7).

On the other hand, the system control unit 13 that has received the imaging mode start instruction signal input through the input unit 12 generates first image data for positional deviation correction by supplying the X-ray irradiation conditions in the positional deviation correction imaging mode, which are stored in the input information storage unit of the system control unit 13, and the newly generated X-ray generation instruction signal to the high voltage control unit 51 of the high voltage generation unit 5 (step S5 in FIG. 7).

Then, the device information detection unit 91 of the display data generation unit 9 performs smoothing processing, contour extraction processing, and matching processing on the first image data for positional deviation correction, which is supplied from the image data generation unit 8, and detects the treatment device information of the image data (step S6 in FIG. 7).

Then, the correction data generation unit 93 of the display data generation unit 9 detects the positional deviation of treatment device position information for the treatment device information by comparing the treatment device information of the image data for positional deviation correction, which is supplied from the device information detection unit 91, with the position information of the treatment device, which is supplied from the position information acquisition unit 92, generates correction data for correcting the positional deviation for the position information of the treatment device on the basis of this detection result, and stores the correction data in the correction data storage unit of the correction data generation unit 93 (step S7 in FIG. 7).

Then, the position information correction unit 94 of the display data generation unit 9 corrects the positional deviation for the position information of the treatment device, which is supplied from the position information acquisition unit 92, using the correction data read from the correction data storage unit of the correction data generation unit 93 (step S8 in FIG. 7). The data combination unit 95 generates first display data for treatment device monitoring by superimposing the position information of the treatment device whose positional deviation has been corrected by the position information correction unit 94 on the reference image data read from the image data storage unit of the image data generation unit 8 and displays the first display data for treatment device monitoring on the monitor of the display unit 10 (step S9 in FIG. 7).

Then, when it is determined that the treatment device inserted into the body of the patient 300 has not yet reached a desired position by observation of the first display data for treatment device monitoring displayed on the display unit 10, the operator inserts the treatment device further, and the position information acquisition unit 92 of the display data generation unit 9 acquires the position information of the treatment device that is newly supplied from the position detector 200 of the treatment device at this time (step S10 in FIG. 7).

On the other hand, the elapsed time measurement unit 111 of the imaging timing setting unit 11 measures an elapsed time from the imaging mode start instruction signal in the positional deviation correction imaging mode, which is supplied through the system control unit 13 from the input unit 12 (step S11 in FIG. 7). If the elapsed time does not reach the predetermined time $\Delta\tau$, the elapsed time measurement unit 111 sequentially performs the generation and display of the display data for treatment device monitoring subsequent to the first display data for treatment device monitoring, the insertion of the treatment device and the acquisition of the treatment device position information, and the measurement of elapsed time by repeating steps S8 to S11 described above.

On the other hand, if the elapsed time reaches the predetermined time $\Delta\tau$ in step S11, the elapsed time measurement unit 111 supplies the imaging timing signal to the high voltage generation unit 5 of the X-ray imaging unit 1 and generates new image data for positional deviation correction and updates correction data based on the image data for positional deviation correction by repeating steps S5 to S11, and then sequentially performs the generation and display of the display data for treatment device monitoring, the insertion of the treatment device and the acquisition of the treatment device position information, and the measurement of elapsed time in the same procedure described above.

In addition, when it is determined that the treatment device inserted into the body of the patient 300 has reached a desired position by observation of the display data for treatment device monitoring displayed on the display unit 10 in step S9, the X-ray imaging in the positional deviation correction imaging mode is ended (step S12 in FIG. 7).

In addition, in the measurement of the elapsed time in step S11 when generating and displaying time-series display data for treatment device monitoring by repeating steps S5 to S11 or steps S8 to S11, measurement of the elapsed time according to the imaging timing signal, which is supplied from the imaging timing setting unit 11 when the newest image data for positional deviation correction is generated, is preferable. However, as already described, when generating second image data for positional deviation correction subsequent to the first image data for positional deviation correction, measurement of the elapsed time according to the imaging start signal supplied from the input unit 12 is preferable.

According to the above-described embodiment of the invention, when the position information of the treatment device measured separately is displayed so as to be superimposed on the reference image data collected by the X-ray imaging in the stationary imaging mode, it is possible to give the accurate position information of the treatment device to the reference image data by correcting the positional deviation for the position information of the treatment device on the basis of the treatment device information of the image data for positional deviation correction collected by the X-ray imaging in the positional deviation correction imaging mode.

In addition, since the image data for positional deviation correction is collected by low-rate or intermittent X-ray imaging in the positional deviation correction imaging mode, it is possible to significantly reduce the exposure dose to a patient.

In addition, since the X-ray irradiation range in the positional deviation correction imaging mode in the present embodiment is determined by the movable diaphragm whose position is controlled on the basis of the position information of the treatment device supplied from the position detector of the treatment device inserted into the body of the patient, it becomes easy to limit the above-described X-ray irradiation range to the relatively narrow range around the treatment device. Therefore, it is possible to further reduce the exposure dose to a patient.

In addition, since the imaging timing in the positional deviation correction imaging mode is determined by the elapsed time from the preceding imaging timing, the movement speed of the treatment device, the size of correction data, the positional relationship between the treatment device and the region of interest in the blood vessel, and the like, accurate positional deviation correction of the treatment device position information can be performed with a less number of X-ray imaging.

While the embodiment of the invention has been described, the invention is not limited to the above-described embodiment, and modifications may be made without being limited to the above-described embodiment. For example, although the case where the X-ray imaging in the positional deviation correction imaging mode for a desired direction is performed by moving the first imaging system, which is fixed to the floor type holding unit, around the patient has been described in the above embodiment, X-ray imaging in the positional deviation correction imaging mode may be performed by first and second imaging systems using a so-called biplane type X-ray imaging unit that further includes a second imaging system fixed to a ceiling traveling type holding unit or the like. For example, when the reference image data collected in the stationary imaging mode is road map image data having three-dimensional information, the position information of the treatment device whose positional deviation has been corrected in a three-dimensional manner using the image data for positional deviation correction, which has been collected from several different directions by the above-described biplane X-ray imaging, may be added to the reference image data and the result may be displayed.

In addition, although the case where the X-ray irradiation range in the positional deviation correction imaging mode is set on the basis of the position information of the treatment device supplied from the position detector 200 has been described in the above embodiment, the X-ray irradiation range may also be set on the basis of the treatment device information of the image data for positional deviation correction detected by the device information detection unit 91 of the display data generation unit 9.

In addition, in the above embodiment, the case has been described in which, when controlling the X-ray irradiation conditions such that the average pixel value of the image data for positional deviation correction becomes a predetermined value, subsequent image data for positional deviation correction is collected according to the X-ray irradiation conditions updated on the basis of the average pixel value of the preceding image data for positional deviation correction. However, the subsequent image data for positional deviation correction may also be collected according to the X-ray irradiation conditions set/updated on the basis of the average pixel value of a region corresponding to the image data for positional deviation correction in the reference image data in the stationary imaging mode or in the image data in other imaging modes, such as a fluoroscopic imaging mode. In addition, the X-ray irradiation conditions may be set/updated on the basis of the maximum pixel value instead of the average pixel value of the region.

In addition, although the case where the position detector 200 is provided in a treatment device, such as a stent or a guide wire inserted into the blood vessel, has been described in the above embodiment, the position detector 200 may also be provided at the distal end of the catheter, which is used for the insertion of the treatment device, or in a treatment device used for DCA (Directional Coronary Atherectomy).

In addition, each unit included in the X-ray image diagnostic apparatus 100 according to the present embodiment may also be realized by using a computer, which is configured to include a CPU, a RAM (Random Access Memory), a magnetic storage device, an input device, and a display device, as hardware, for example. For example, the system control unit 13 of the X-ray image diagnostic apparatus 100 may realize various functions by making a processor, such as a CPU mounted in the computer, execute a predetermined control program. In this case, the above-described control program may be installed in the computer in advance. Alternatively, a control program, which is stored in a computer-readable medium or distributed through a network, may be installed in the computer.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. An X-ray image diagnostic apparatus comprising:
    an X-ray imager configured to generate projection data by performing X-ray imaging in first and second imaging modes for a patient;
    an image data generation processor configured to generate reference image data based on projection data in the first imaging mode and image data for positional deviation correction based on projection data in the second imaging mode, the second imaging mode utilizing low-rate or intermittent X-ray imaging compared to the first imaging mode;
    a position information acquisition processor configured to acquire position information of a treatment device inserted into a body of the patient;
    a position information correction processor configured to correct the position information of the treatment device on the basis of the position information of the treatment device and treatment device information of the image data for positional deviation correction, which is collected by X-ray imaging in the second imaging mode utilizing low-rate or intermittent X-ray imaging for the patient to whom the treatment device has been inserted;
    a display configured to display the reference image data to which the corrected position information is added; and an imaging timing setting processor configured to set an imaging timing in the second imaging mode on the basis of measurement results using measurement functions, wherein the imaging timing setting processor includes at least one of an elapsed time measurement function of measuring an elapsed time from a start instruction signal of the second imaging mode or a preceding imaging timing signal, a device movement speed measurement function of measuring a movement speed of the treatment device, and a correction data measurement function of measuring a size of correction data.

2. The X-ray image diagnostic apparatus according to claim 1, further comprising:

a correction data generation processor configured to generate correction data on the basis of the position information of the treatment device and the treatment device information of the image data for positional deviation correction, wherein the position information correction processor corrects a positional deviation for the treatment device information of the position information, which is supplied in time series from the treatment device, using the correction data.

3. The X-ray image diagnostic apparatus according to claim 1, further comprising:

a data combination processor configured to generate display data for treatment device monitoring to check a position of the treatment device by superimposing corrected position information of the treatment device on the reference image data, wherein the display displays the display data for treatment device monitoring generated by the data combination processor.

4. The X-ray image diagnostic apparatus according to claim 1, further comprising:

a diaphragm moving mechanism that sets an X-ray irradiation range in the first imaging mode and an X-ray irradiation range in the second imaging mode for the patient and a moving mechanism control processor configured to control movement of the diaphragm moving mechanism, wherein the moving mechanism control processor forms the X-ray irradiation range in the second imaging mode, which is smaller than the X-ray irradiation range in the first imaging mode including the treatment device, by moving the diaphragm moving mechanism in a predetermined direction on the basis of the position information of the treatment device.

5. The X-ray image diagnostic apparatus according to claim 1, wherein the imaging timing setting processor has at least one of a contrast agent injection period determination function of determining a period, for which a contrast agent is injected into the body of the patient, and a positioning setting period determination function of determining a setting period of an imaging position or an imaging direction for the patient, and stops a setting of the imaging timing on the basis of determination results using the determination functions.

6. The X-ray image diagnostic apparatus according to claim 1, further comprising:

an instruction signal input configured to input an imaging instruction signal when the treatment device is close to a region of interest of the patient, wherein the imaging timing setting processor sets the imaging timing in the second imaging mode on the basis of the imaging instruction signal.

7. The X-ray image diagnostic apparatus according to claim 1, further comprising:

a pixel value measurement processor configured to measure a pixel value in an evaluation region having a predetermined size based on image data for positional deviation correction collected in advance or treatment device information of the image data for positional deviation correction; and an X-ray irradiation condition update processor configured to update X-ray irradiation conditions, which are set in advance for image data for positional deviation correction subsequent to the image data for positional deviation correction, on the basis of a measurement result of the pixel value.

8. The X-ray image diagnostic apparatus according to claim 1, wherein the X-ray imager performs X-ray imaging in the first imaging mode for the patient to whom a contrast agent is injected, and performs X-ray imaging in the second imaging mode for the patient to whom the treatment device is inserted.

9. The X-ray image diagnostic apparatus according to claim 1, wherein the position information acquisition processor acquires the position information of the treatment device using a GPS.

10. The X-ray image diagnostic apparatus according to claim 1, further comprising:

a magnetic field generator that generates a magnetic field, wherein the position information acquisition processor acquires the position information of the treatment device on the basis of a signal based on a detected magnetic field from the treatment device having a magnetic sensor that detects the magnetic field generated by the magnetic field generator.

* * * * *